(12) United States Patent
Lockhart et al.

(10) Patent No.: US 8,703,049 B2
(45) Date of Patent: Apr. 22, 2014

(54) APPARATUS AND METHOD OF IMPROVING AIR QUALITY USING PHOTOCATALYTIC OXIDATION

(75) Inventors: Frank Lockhart, Florence, SC (US); Timothy Matt, Pinehurst, NC (US); Joseph DeAngelis, Wheaton, IL (US); Dennis Neibrook, Florence, SC (US)

(73) Assignee: Marley Engineered Products LLC, Bennettsville, SC (US)

( * ) Notice: Subject to any disclaimer, the term of this patent is extended or adjusted under 35 U.S.C. 154(b) by 633 days.

(21) Appl. No.: 12/472,751

(22) Filed: May 27, 2009

(65) Prior Publication Data
US 2010/0303678 A1  Dec. 2, 2010

(51) Int. Cl.
*A61L 9/00* (2006.01)
*A61L 2/00* (2006.01)
*A62B 7/08* (2006.01)
*G01N 21/00* (2006.01)

(52) U.S. Cl.
USPC ........... 422/24; 42/1; 42/5; 42/121; 42/186.3; 250/453.11; 250/492.1; 96/224; 96/225

(58) Field of Classification Search
USPC ................... 422/1, 5, 24, 121, 186.04, 186.3; 250/453.11, 455.11, 492.1; 96/224, 96/225
See application file for complete search history.

(56) References Cited

U.S. PATENT DOCUMENTS

| 2002/0094298 A1* | 7/2002 | Monagan | 422/5 |
| 2005/0269254 A1 | 12/2005 | Roitmas | |
| 2006/0127288 A1 | 6/2006 | Hay et al. | |
| 2007/0253860 A1* | 11/2007 | Schroder | 422/4 |
| 2009/0010801 A1 | 1/2009 | Murphy et al. | |

FOREIGN PATENT DOCUMENTS

| CN | 1834542 A | 9/2006 |
| CN | 201138022 Y | 10/2008 |

* cited by examiner

*Primary Examiner* — Monzer R Chorbaji
(74) *Attorney, Agent, or Firm* — Baker & Hostetler LLP

(57) ABSTRACT

An apparatus and a method for purifying and heating air using photocatalytic oxidation. The apparatus includes a housing, a heater, and a photocatalytic oxidation unit disposed within the housing. The housing defines a flow path for air to move through the apparatus such that air from the environment is drawn into the apparatus and passes over the photocatalytic oxidation unit. A pollutant in the air from the environment adsorbs to a surface of the photocatalytic material coating the plates, and the surface of the photocatalytic material is exposed to ultraviolet light generated by the ultraviolet light source. The energy of the ultraviolet light activates the photocatalytic material, which then breaks down the pollutant leaving non-toxic components and purified air. The air then passes over the heater and back into the environment. A fan is also included to move air through the flow path.

20 Claims, 5 Drawing Sheets

APPARATUS AND METHOD OF IMPROVING AIR QUALITY USING PHOTOCATALYTIC OXIDATION

FIELD OF THE INVENTION

The invention relates generally to a method and apparatus for heating and purifying air within a room. More particularly, the invention relates to heating and purifying air within a room using resistance heat or radiant heat or any other suitable heating apparatus and photocatalytic oxidation respectively.

BACKGROUND OF THE INVENTION

Air includes contaminants such as mold, pollen, dust, pet dander, and other particles that can cause mild to severe allergic reactions. Air purifiers have been used to remove these contaminants from the air in people's homes and businesses and alleviate the symptoms associated with allergies and asthma. Several different processes are used in air purifiers to remove the contaminants from the air. One such process uses an air filter that physically traps particles in the air and that pass over the filter.

Another process more recently developed for use in air purifiers is photocatalytic oxidation. Photocatalytic oxidation is the process of irradiating a semi-conductor photocatalyst using short-wave ultraviolet light, generally having a wavelength of less than 385 nanometers. Irradiating the photocatalyst causes a band gap energy to be exceeded and an electron to be promoted from the valence band to the conductive band resulting in an electron-hole pair ($h^+$ and $e^-$). The $h^+$ and $e^-$ can react with organic compounds, and the organic compound is oxidized or reduced. For instance, if a molecule which favors giving up an electron, such as ethanol, methanol, or water, is present on the photocatalyst, then the photo-generated hole ($h^+$) can react with the organic compound to generate an oxidized product. The hole accepts the electron and the molecule becomes an electron poor, high energy intermediate. Similarly, if there is an electron acceptor, such as oxygen or hydrogen peroxide and is present on the photocatalyst, then the photo-generated conductance band electrons ($e^-$) can react with it to generate a reduced product. The electron poor molecule accepts the electron from the conduction band and the molecule becomes an electron rich, high energy intermediate. In a complete photocatalytic oxidation reaction, the final products are $CO_2$ and $H_2O$. While air purifiers are extremely useful for a home or commercial user, air purifiers occupy additional space when used with a space heater.

These and other drawbacks exist with current systems.

SUMMARY OF THE INVENTION

The foregoing disadvantages are overcome, to a great extent, by the invention, wherein in one aspect, an apparatus is provided that in some embodiments provides an apparatus and a method for purifying and heating air using photocatalytic oxidation including a housing, a heater, and a photocatalytic oxidation unit including plates coated with a photocatalytic material and an ultraviolet light source disposed within the housing. The housing defines a flow path for air to move through the apparatus such that air from the environment is drawn into the apparatus and passes over the photocatalytic oxidation unit.

A photocatalytic reaction occurs when a pollutant in the air from the environment adsorbs to a surface of the photocatalytic material coating the plates. The surface of the photocatalytic material is exposed to ultraviolet light generated by the ultraviolet light source. The energy of the ultraviolet light activates the photocatalytic material, which then breaks down the pollutant leaving non-toxic components and purified air. The air then passes over the heater and back into the environment. A fan may be included to move air through the flow path.

In accordance with an aspect of the invention, an air purifying heating apparatus includes a housing having an interior space defined by walls of the housing and a heater disposed within the housing. The heater may be, for example, a low wattage electric radiant heater or a low wattage resistive heater. The housing also defines an air intake and an air outlet. An ultra-violet light source and plates coated with a photocatalytic material may also be positioned within the interior space of the housing such that light generated by the ultraviolet light source illuminates a surface of the plates.

A flow path is defined by the housing such that air travels into the air purifying heating apparatus and over the plates illuminated by the ultra-violet light and out of the air purifying heating apparatus. The air travels over the plates, so that pollutants in the air adsorb to the surface of the photocatalytic material coating the plates. Energy from the ultraviolet light causes a band gap energy to be exceeded and an electron to be promoted from a valence band to a conductive band, resulting in an electron-hole pair ($h^+$ and $e^-$). The $h^+$ and $h^-$ can react with organic compounds, and the organic compound is oxidized or reduced. For instance, if a molecule which favors giving up an electron, such as ethanol, methanol, or water, is present on the plates, then the photo-generated hole ($h^+$) can react with the organic compound to generate an oxidized product. The hole accepts the electron and the molecule becomes an electron poor, high energy intermediate. Similarly, if there is an electron acceptor, such as oxygen or hydrogen peroxide and is present on the plates, then the photo-generated conductance band electrons ($e^-$) can react with it to generate a reduced product. The electron poor molecule accepts the electron from the conduction band and the molecule becomes an electron rich, high energy intermediate. In a complete photocatalytic oxidation reaction, the final products are $CO_2$, $H_2O$, and purified air. Additionally, a fan may be positioned within the housing and configured to move air through the flow path.

In accordance with another aspect of the invention, the air purifying heating apparatus may include an ultraviolet light bulb or a plurality of ultraviolet light bulbs producing ultraviolet light with a wavelength between, for example, 200 nm and 400 nm. More specifically, the ultraviolet light source may generate light having a wavelength of 254 nm. The air purifying heating apparatus may include a single plate or a plurality of plates coated with the photocatalytic material, and the photocatalytic coating on the plates may be, for example, titanium dioxide.

In accordance with yet another aspect of the invention, a method of manufacturing an air purifying heating apparatus includes providing a housing having an interior space defined by walls of the housing. The housing may include an air intake and an air outlet. The method may also include positioning a heater, an ultra-violet light source, and plates coated with a photocatalytic material within the interior space of the housing such that light generated by the ultra-violet light source illuminates a surface of the plates.

Additionally, the method includes creating a flow path defined by the housing such that air travels into the air purifying apparatus and over the plates illuminated by the ultraviolet light. The air travels over the plates, so that pollutants in the air adsorb to the surface of the photocatalytic material coating the plates. ($h^+$ and $e^-$). The $h^+$ and $e_-$ can react with organic compounds, and the organic compound is oxidized or reduced. For instance, if a molecule which favors giving up an electron, such as ethanol, methanol, or water, is present on the plates, then the photo-generated hole ($h^+$) can react with the organic compound to generate an oxidized product. The hole accepts the electron and the molecule becomes an electron poor, high energy intermediate. Similarly, if there is an electron acceptor, such as oxygen or hydrogen peroxide and is present on the plates, then the photo-generated conductance band electrons ($e^-$) can react with it to generate a reduced product. The electron poor molecule accepts the electron from the conduction band and the molecule becomes an electron rich, high energy intermediate. In a complete photocatalytic oxidation reaction, the final products are $CO_2$, $H_2O$, and purified air. A fan may be positioned within the housing configured to move air through the flow path.

In accordance with another aspect of the invention, the method includes using an ultra-violet light source including an ultraviolet light emitting bulb or a plurality of ultraviolet light emitting bulbs generating light with a wavelength between 200 nm and 400 nm. The photocatalytic material can take the form of titanium dioxide and the plates may include a single plate or a plurality of plates coated with the photocatalytic material. Additionally the heater can take the form of an electric radiant, resistive heater, or any other suitable heating apparatus.

In accordance with another aspect of the invention, an air purifying heating apparatus includes means for generating heat and means for housing the means for generating heat. The air purifying heating apparatus may also include means for generating ultra-violet light disposed within the means for housing. Additionally, means for providing a photocatalytic material is positioned within the means for housing, such that light generated by the means for generating ultra-violet light illuminates a surface of the plates.

The air purifying heating apparatus may further include means to move air through the housing, such that air travels into the air purifying apparatus and over the means for providing a photocatalytic material. Pollutants in the air adsorb to the means for providing a photocatalytic material. The means for providing a photocatalytic material is illuminated by the means for generating ultra-violet light, and energy from the ultraviolet light causes a band gap energy to be exceeded and an electron to be promoted from a valence band to a conductive band, resulting in an electron-hole pair ($h^+$ and $e^-$). The $h^+$ and $e^-$ can react with organic compounds, and the organic compound is oxidized or reduced. For instance, if a molecule which favors giving up an electron, such as ethanol, methanol, or water, is present on the plates, then the photo-generated hole ($h^+$) can react with the organic compound to generate an oxidized product. The hole accepts the electron and the molecule becomes an electron poor, high energy intermediate. Similarly, if there is an electron acceptor, such as oxygen or hydrogen peroxide and is present on the plates, then the photo-generated conductance band electrons ($e^-$) can react with it to generate a reduced product. The electron poor molecule accepts the electron from the conduction band and the molecule becomes an electron rich, high energy intermediate. In a complete photocatalytic oxidation reaction, the final products are $CO_2$, $H_2O$, and purified air.

There has thus been outlined, rather broadly, certain embodiments of the invention in order that the detailed description thereof herein may be better understood, and in order that the contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the invention. It is important, therefore, that the claims be regarded as including such equivalent constructions insofar as they do not depart from the spirit and scope of the invention.

DETAILED DESCRIPTION

Figure 1:
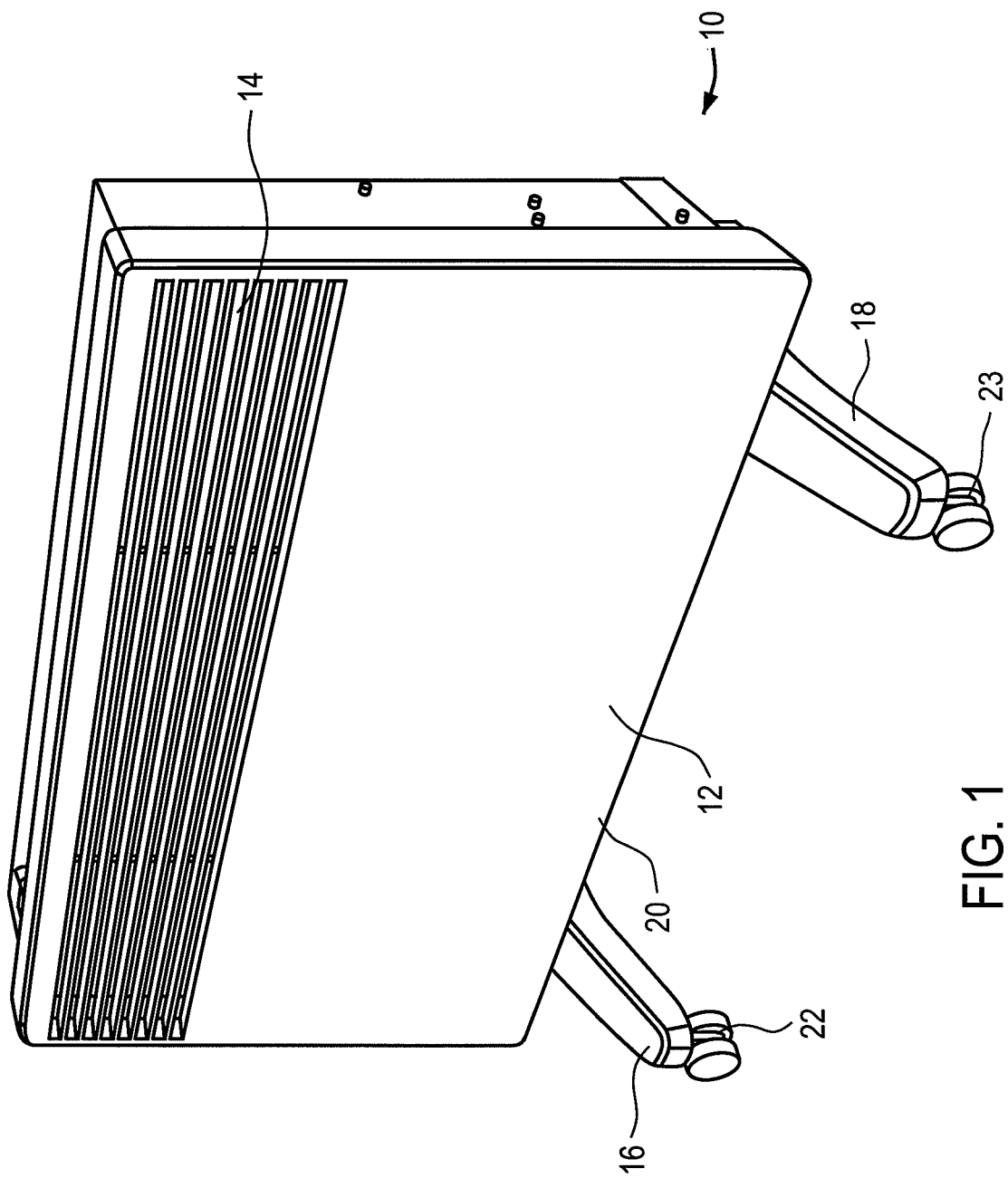
FIG. 1 illustrates an air purifying heating apparatus in accordance with an embodiment of the invention.

The invention will now be described with reference to the drawing figures, in which like reference numerals refer to like parts throughout. An embodiment in accordance with the invention provides an apparatus and a method for purifying air using photocatalytic oxidation and also heating the air.

FIG. 1 illustrates an air purifying heating apparatus 10 in accordance with an embodiment of the invention. The air purifying heating apparatus 10 includes a front cover 12 having outlet vents 14. As illustrated, the outlet vents 14 cover only a portion of the front cover 12, however, the outlet vents 14 may be configured in any suitable manner. The air purifying heater apparatus may also include supports 16, 18. The supports 16, 18 may be mounted on a bottom surface 20 of the air purifying heating apparatus 10. The supports 16, 18 may be used to elevate the air purifying heating apparatus 10 from a surface upon which it is sitting. Casters 22, 23 may be mounted on supports 16, 18, respectively, to facilitate the mobility of the air purifying heating apparatus 10.

Figure 2:
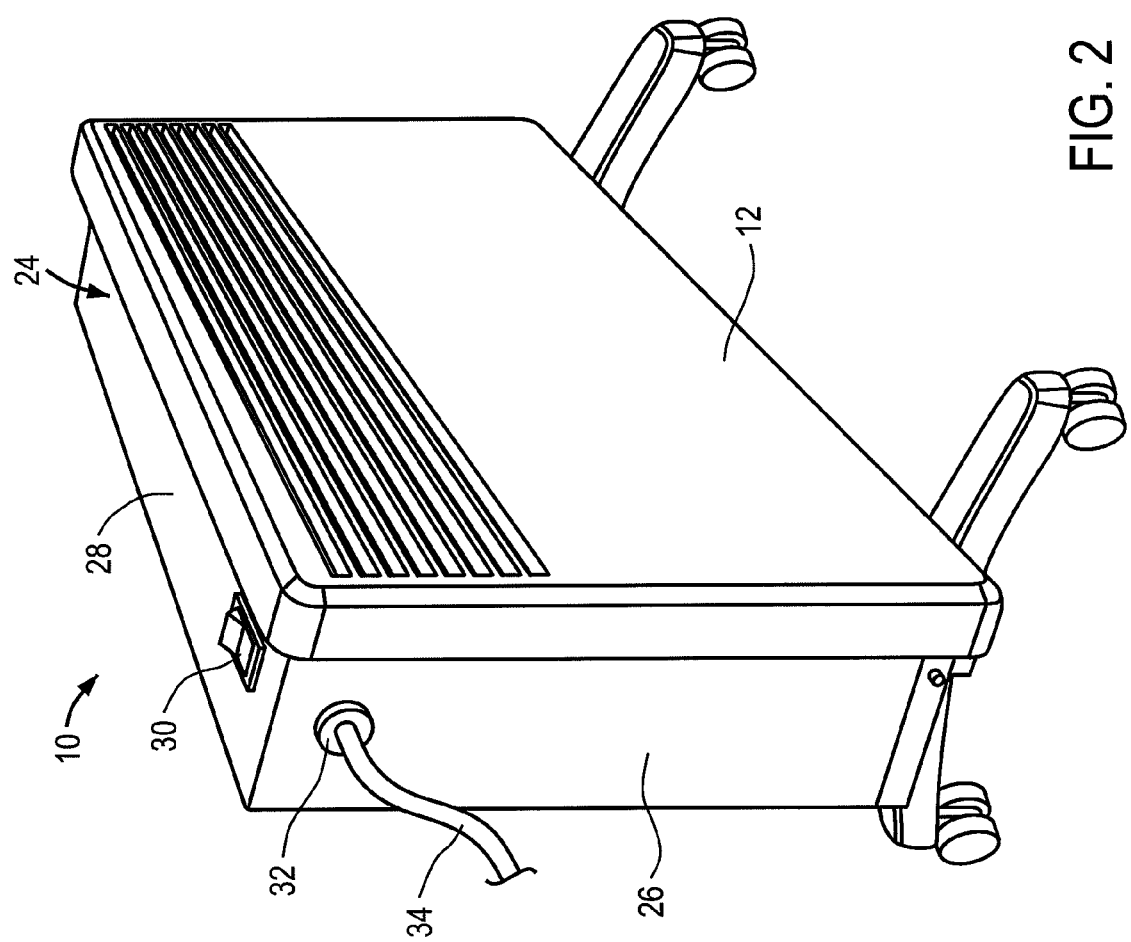
FIG. 2 is a perspective view of an air purifying heating apparatus in accordance with an embodiment of the invention.

FIG. 2 is a perspective view of the air purifying heating apparatus 10 in accordance with an embodiment of the invention. The air purifying heating apparatus 10 includes a housing 24. As illustrated, the housing 24 is generally rectangular in shape, although other shapes may also be used. The housing includes sides 26, 28 that accommodate internal components of the air purifying heating apparatus 10. The front cover 12 is mounted to a front side of the housing 24.

Control electronics and/or an on off switch 30 is also mounted on the side 28 of the housing 24, but may be mounted in any suitable position on the housing 24 of the air purifying heating apparatus 10. The on/off switch 30 may be configured to control heating and air purifying capabilities of the air purifying heating apparatus 10. For example, the heating capabilities may be turned on while the air purifying capabilities are turned off, or the heating capabilities may be turned off while the air purifying capabilities are turned on. Additionally, both the heating and air purifying capabilities may be turned on or off simultaneously. The housing 24 also defines an opening 32 such that a power cord 34 may extend through the opening 32, to provide power to the internal components of the air purifying heating apparatus 10.

Figure 3:
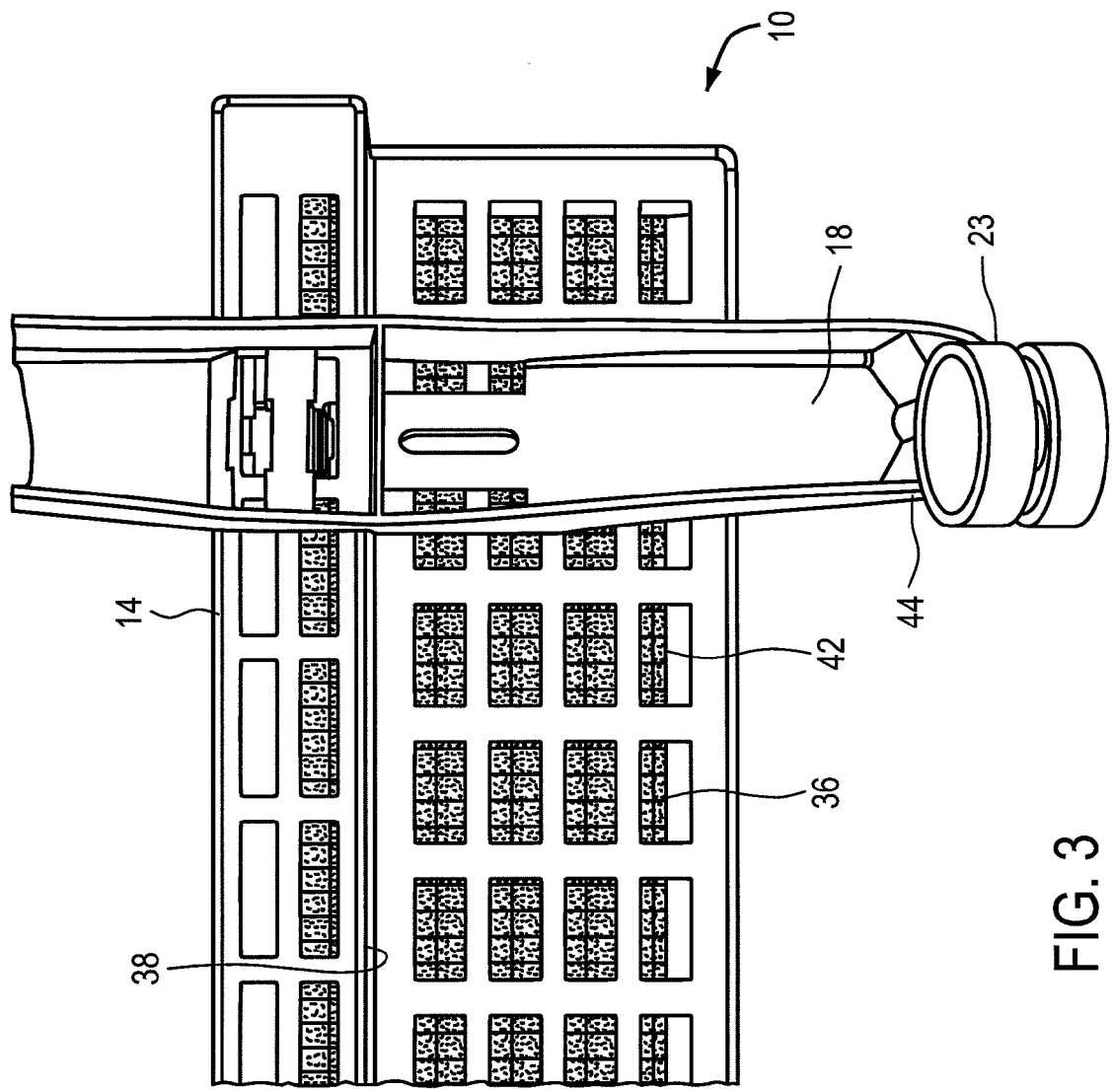
FIG. 3 is a perspective view of an air purifying heating apparatus in accordance with an embodiment of the invention.

FIG. 3 is a perspective view of the air purifying heating apparatus 10 in accordance with an embodiment of the invention. FIG. 3 illustrates an underside 36 of the air purifying heating apparatus 10. The front cover 14 is mounted to a lip 38 of the housing 24. Both the front cover 14 and the housing 24 define air intake openings 42 that allow air from the environment to enter the air purifying heating apparatus 10 to be purified and heated. The support 18 may be fixedly attached to the underside 36 of the air purifying heating apparatus 10. The support 18 elevates the underside 36 of the air purifying heating apparatus 10 up from the surface upon which it is sitting such that air may flow into the air intake openings 42. Caster 23 is mounted on an outer edge 44 of the support 18 to give the air purifying heating apparatus more mobility.

Figure 4:
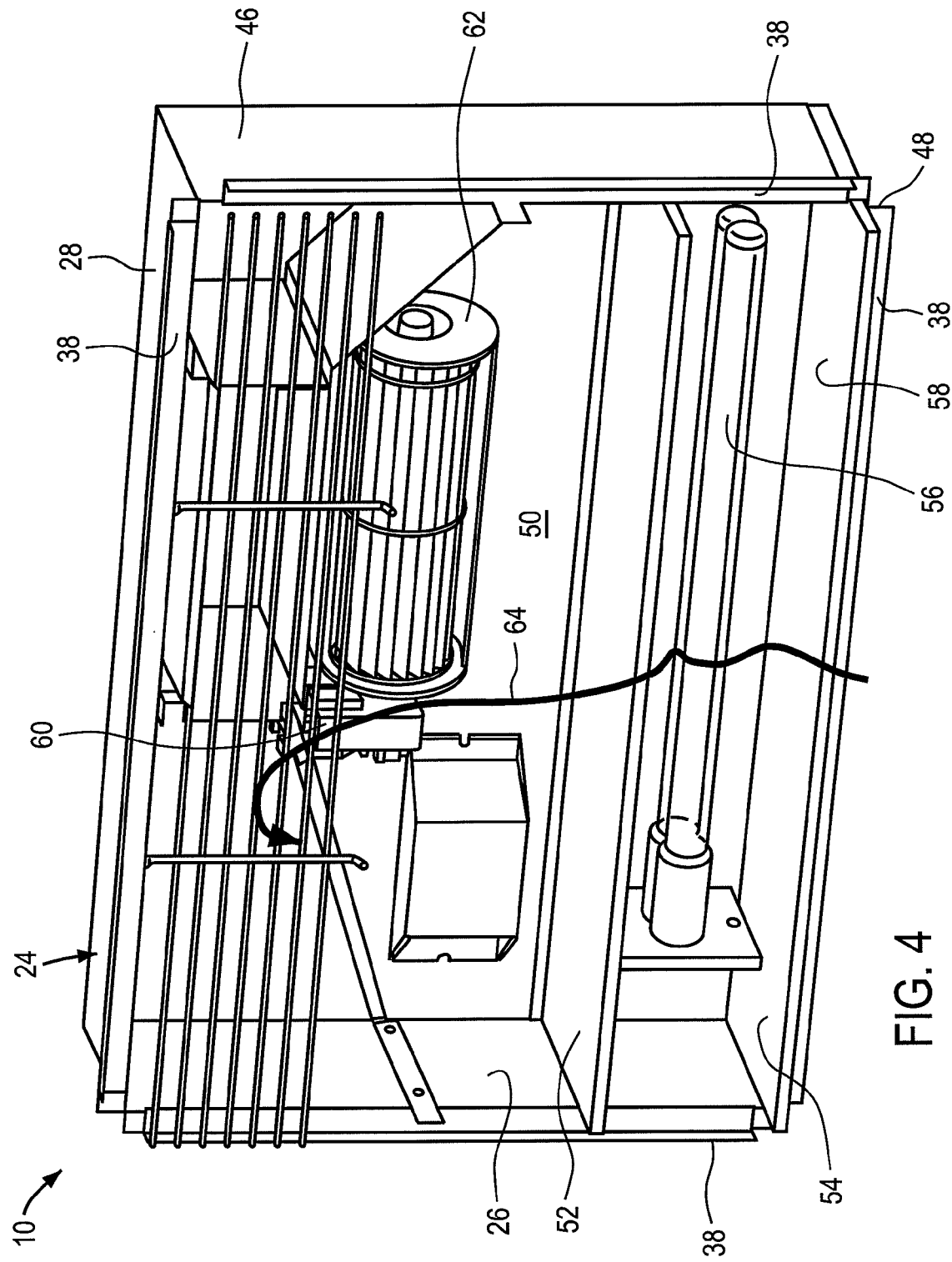
FIG. 4 is a sectional view of an air purifying heating apparatus in accordance with an embodiment of the invention.

FIG. 4 is a sectional view of the air purifying heating apparatus 10 in accordance with an embodiment of the invention. The housing 24 includes sides 26, 28, 46, and 48 that define an interior space 50. Each of the sides 26, 28, 46, and 48 have a lip 38 to which the front cover 14 (shown in FIG. 1) is attached. Plates 52, 54 are disposed within the interior space 50 of the housing 24. The plates 52, 54 are coated with a photocatalytic material such as, for example, titanium dioxide, however, any other suitable photocatalyst may be used. An ultraviolet light source 56 is also disposed within the interior space 50 of the housing 24. As illustrated in FIG. 4, the ultraviolet light source 56 includes two ultraviolet light bulbs, but any suitable number of bulbs may be used. The ultraviolet light source 56 may be mounted between plates 52, 54, however, any configuration may be used as long as ultraviolet light shines on a surface 58 of plates 52, 54. Additionally, a heater 60 is disposed within the interior space 50 of the housing 24, and a fan 62 is positioned adjacent to the heater 60.

As illustrated in FIG. 4, the housing 24 defines a flow path 64 such that air from the environment enters the air purifying heating apparatus 10. The flow path 64 is further defined such that the air travels over plates 52, 54 coated with the photocatalytic material and illuminated by the ultraviolet light source 56. As the air travels over the plates 52, 54 pollutants such as volatile organic compounds, in the air are oxidized by a photocatalytic reaction. The photocatalytic reaction occurs when the pollutant adsorbs to a surface of the photocatalytic material coating plates 52, 54 and is exposed to ultraviolet light generated by the ultraviolet light source 56. The energy of the ultraviolet light activates the photocatalytic material, which then breaks down the pollutant leaving non-toxic components and purified air. Preferably, the ultraviolet light source 56 generates ultraviolet light with a wavelength of substantially between 200 nm and 400 nm and more specifically, of approximately 254 nm. The plates 52, 54 may be coated with titanium dioxide or any other suitable photocatalytic material.

The fan 62 moves air through the flow path 64 and over the heater 60. The heater 60 warms the purified air before it exits the air purifying heating apparatus 10 through the outlet vents 14. The heater 60 may be a radiant heater, a resistive heater, or any other suitable heating apparatus.

Figure 5:
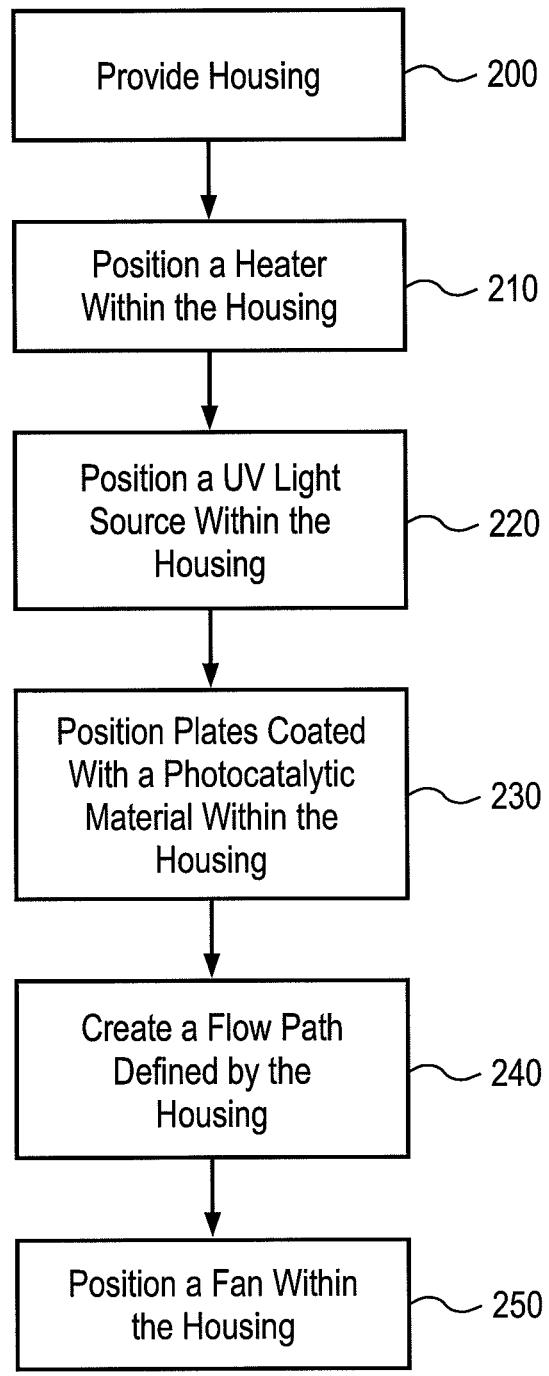
FIG. 5 is a flow chart illustrating a method of manufacture of the air purifying heating apparatus in accordance with an embodiment of the invention.

FIG. 5 is a flow chart illustrating a method of manufacturing an air purifying heating apparatus in accordance with an embodiment of the invention. The method includes a step 200 of providing a housing for the air purifying heating apparatus. The housing may take any suitable shape or size and defines an air intake and an air outlet. Another step 210 includes positioning a heater within the housing. The heater preferably is an electric radiant or resistive heater, but may be any other suitable heating apparatus. Step 220 includes positioning an ultraviolet light source within the housing. The ultraviolet light source can include two ultraviolet light generating bulbs or any other number of bulbs. The ultraviolet light generating bulbs preferably generate light having a wavelength between 200 nm and 400 nm and more preferably a wavelength of 254 nm.

Step 230 includes positioning plates coated with a photocatalytic material within the housing. Preferably, two plates are used, but any suitable number of plates may be positioned within the housing. The plates are coated with a photocatalytic material such as titanium dioxide. Another step 240, includes creating a flow path defined by the housing, such that air enters the air purifying apparatus and passes over the plates illuminated by the ultra-violet light. Step 250 includes positioning a fan configured to move air through the flow path within the housing.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. An air purifying heating apparatus comprising:
a housing having an interior space defined by walls of the housing;
a support configured to elevate the housing above a support surface;
a heater disposed within the housing;
an ultra-violet light source disposed within the interior space of the housing and having a longitudinal axis defined along a longest length of the ultra-violet light source;
at least two plates coated with a photocatalytic material positioned within the interior space of the housing at two different positions with respect to the ultra-violet light source such that light generated by the ultra-violet light source illuminates at least one surface of each of the at least two plates and wherein the at least one surface of each of the at least two plates illuminated by the ultra-violet light source define substantially parallel, non-intersecting planes, and are parallel to the longitudinal axis of the ultra-violet light source;
a flow path defined by the housing such that air travels into the air purifying apparatus and first over one of the at least two plates illuminated by the ultra-violet light, next past the ultra-violet light, and subsequently past another one of the at least two plates and out of the air purifying apparatus; and a fan disposed within the interior space of the housing and configured to move air through the flow path.

2. The air purifying heating apparatus of claim 1, wherein the photocatalytic material comprises titanium dioxide.

3. The air purifying heating apparatus of claim 1, wherein the ultra-violet light source comprises an ultra-violet light emitting bulb.

4. The air purifying heating apparatus of claim 1, wherein the at least two plates are arranged on opposite sides of the ultra-violet light source.

5. The air purifying heating apparatus of claim 1, wherein the housing comprises an air intake arranged at a lower end of the housing and the support configured to elevate the housing above the support surface includes casters.

6. The air purifying heating apparatus of claim 1, wherein the housing comprises an air outlet arranged at an upper end of the housing, wherein air moves substantially vertically through the housing and out the air outlet.

7. The air purifying heating apparatus of claim 1, wherein the ultraviolet light source emits ultra-violet light with a wavelength substantially between 200 nm and 400 nm.

8. The air purifying heating apparatus of claim 7 wherein the ultraviolet light source emits light with a wavelength of 254 nm.

9. The air purifying heating apparatus of claim 1, wherein the heating element comprises any one of a resistive heater, radiant heater, or any other suitable heating apparatus.

10. A method of manufacturing an air purifying heating apparatus comprising:
  providing housing having an interior space defined by walls of the housing;
  providing a support configured to elevate the housing above a support surface;
  positioning a heater within the interior space of the housing;
  positioning an ultra-violet light source within the interior space of the housing having a longitudinal axis defined along a longest length of the ultra-violet light source;
  positioning at least two plates coated with a photocatalytic material within the interior space of the housing at two different positions with respect to the ultra-violet light source such that light generated by the ultra-violet light source illuminates at least one surface of each of the at least two plates and wherein the at least one surface of each of the at least two plates illuminated by the ultra-violet light source define substantially parallel, non-intersecting planes and are substantially parallel to the longitudinal axis of the ultra-violet light source;
  creating a flow path defined by the housing such that air travels into the air purifying apparatus and over one of the at least two plates illuminated by the ultra-violet light, past the ultra-violet light, and past another one of the at least two plates illuminated by the ultra-violet light; and
  positioning a fan within the housing configured to move air through the flow path.

11. The method of claim 10, wherein the ultra-violet light source emits ultra-violet light with a wavelength between 200 nm and 400 nm.

12. The method of claim 10, wherein the photocatalytic material comprises titanium dioxide.

13. The method of claim 10, wherein the ultra-violet light source comprises an ultra-violet light emitting bulb.

14. The method of claim 10, wherein the housing comprises an air intake arranged at a lower end of the housing and the support configured to elevate the housing above the support surface includes casters.

15. The method of claim 10, wherein the housing comprises an air outlet arranged at an upper end of the housing, wherein air moves substantially vertically through the housing and out the air outlet.

16. The method of claim 10, wherein the heating element comprises any one of a radiant heater, resistive heater, or any other suitable heating apparatus.

17. An air purifying heating apparatus comprising:
  means for generating heat;
  means for housing the means for generating heat;
  means for supporting the means for housing at an elevated position above a support surface;
  means, disposed within the means for housing, for generating ultra-violet light having a longitudinal axis defined along its longest length;
  means, disposed within the means for housing, for providing a photocatalytic material at two different positions with respect to the means for generating ultra-violet light such that light generated by the means for generating ultra-violet light illuminates surfaces of the means for providing a photocatalytic material and wherein the illuminated surfaces of the means for providing a photocatalytic material define substantially parallel non-intersecting planes and are arranged parallel to the longitudinal axis, and on opposing sides of and substantially parallel to the means for generating ultra-violet light; and
  means to move air through the means for housing past the means for providing a photocatalytic material, past the means for generating ultra-violet light and then further past another portion of the means for providing a photocatalytic material.

18. The air purifying heating apparatus of claim 17, wherein the means for generating ultraviolet light emits ultra-violet light with a wavelength substantially between 200 nm and 400 nm.

19. The air purifying heating apparatus of claim 17, wherein the means for generating heat comprises any one of a radiant heater, resistive heater, or any other suitable heating apparatus.

20. An air purifying heating apparatus comprising:
  a housing having an interior space defined by walls of the housing;
  a heater disposed within the housing;
  an ultra-violet light source disposed within the interior space of the housing and having a longitudinal axis defined along a longest length of the ultra-violet light source;
  at least two plates coated with a photocatalytic material positioned opposite to one another within the interior space of the housing and at two different positions with respect to the ultra-violet light source such that light generated by the ultra-violet light source illuminates at least one surface of each of the at least two plates and wherein the at least one surface of each of the at least two plates illuminated by the ultra-violet light source define substantially parallel non-intersecting planes and substantially parallel to the longitudinal axis of the ultra-violet light source;
  a flow path defined by the housing such that air travels into the air purifying apparatus and first over one of the at least two plates illuminated by the ultra-violet light, next past the ultra-violet light, and subsequently past another one of the at least two plates; and a fan disposed within the interior space of the housing and configured to move air through the flow path.

* * * * *